United States Patent [19]
Franz

[11] 3,985,031
[45] Oct. 12, 1976

[54] METHOD OF AND APPARATUS FOR SAMPLING MOLTEN SLAG

[75] Inventor: Henry W. Franz, Salt Lake City, Utah

[73] Assignee: Kennecott Copper Corporation, New York, N.Y.

[22] Filed: Aug. 7, 1975

[21] Appl. No.: 602,647

[52] U.S. Cl. .......................... 73/423 R; 73/DIG. 9
[51] Int. Cl.² ........................................... G01N 1/20
[58] Field of Search ............ 73/423 R, 424, DIG. 9, 73/425.4; 427/420

[56] References Cited
UNITED STATES PATENTS

| | | | |
|---|---|---|---|
| 1,521,545 | 12/1924 | Kistler | 73/423 R |
| 2,865,204 | 12/1958 | Lamb | 73/425 |
| 3,524,759 | 8/1970 | McConnell et al. | 427/420 X |
| 3,638,500 | 2/1972 | Wetzel | 73/DIG. 9 |
| 3,717,034 | 2/1973 | Dukelow | 73/DIG. 9 |
| 3,859,857 | 1/1975 | Falk | 73/DIG. 9 |

Primary Examiner—Richard C. Queisser
Assistant Examiner—Daniel K. Yasich
Attorney, Agent, or Firm—Mallinckrodt & Mallinckrodt

[57] ABSTRACT

A method of sampling a stream of molten material, such as slag, matte, or the like, by moving a cooled sampling arm through the stream to pick up a coating of solidified molten material as a sample, and recovering the sample by collecting pieces of the coating as it contracts and breaks apart. Apparatus for carrying out the method comprises a sampling arm, means for cooling the arm, means for moving the cooled arm through a stream of molten material, and means for recovering the broken coating sample. In preferred forms of the apparatus, a hollow sampling arm is internally cooled continuously and comes to rest over a sample recovery bin or other receiving means for recovering the broken pieces of the coating sample as it contracts and the pieces fall off by gravity.

7 Claims, 8 Drawing Figures

METHOD OF AND APPARATUS FOR SAMPLING MOLTEN SLAG

BACKGROUND OF THE INVENTION

1. Field:

This invention is in the field of sampling molten materials.

2. State of the Art:

In many smelting processes it is desirable to sample a slag or matte as it flows in molten condition from a tap hole or down a launder and to subject the samples to various tests. The results of the tests are used to help control the effectiveness of the process. For example, in the smelting of copper, it is desirable to monitor the composition of the slag flowing from the furnace to ensure that the desired chemical reactions have taken place and enough time has been allowed for the slag and matte phases in the furnace to separate satisfactorily. Too much copper sulfide in the slag is an indication of incomplete separation.

The common practice is to manually take a sample from the stream of molten material with a large spoon designed for the purpose. It is important in taking such a sample to cut across the entire cross-section of the stream, but present sampling methods have proven deficient in this respect. Many times the sample will be taken from the most accessible area, which is usually the top of the flowing stream. Even when the complete stream is cut by the spoon, the material caught at the bottom is usually forced out and displaced by material in the upper portion as the spoon is drawn through the stream. A uniform sample is not normally obtained by this method of sampling.

SUMMARY OF THE INVENTION

According to the method of the invention, a cooled sampling arm is moved through the stream of flowing molten material to pick up molten material as a sample and to solidify it as a coating on the sampling arm. The arm is then positioned in a sample recovery area for recovering the coating as it cools, contracts, and breaks away from the sampling arm.

Apparatus for carrying out the method includes a sampling arm provided with means for cooling the arm, means for moving the arm through the molten stream of material to be sampled, and means for recovering the sample as it cools, breaks apart, and falls away from the arm.

In preferred embodiments of the invention, the sampling arm is hollow and pivotally mounted at one of its ends so as to be cooled by circulation of cold water internally thereof. A pneumatically actuated cylinder and piston assembly is connected to a lever arranged so that actuation of the cylinder and lever causes the sample arm to rotate about its pivot axis. The sample collection means comprises a sample-receiving bin disposed under the path of travel of the arm remote from the sample pick-up location. The sweep of the arm in any given instance is of sufficient extent that the sample picked up will solidify, contract, and break into pieces at a conveniently remote location from the sample pick-up location and the receiving bin is located to catch all pieces that break and fall off.

BRIEF DESCRIPTION OF THE DRAWINGS

The invention is described in detail with particular reference to the accompanying drawings, which illustrate embodiments of apparatus representing the best mode presently contemplated of carrying out the invention.

In the drawings.

DETAILED DESCRIPTION OF THE ILLUSTRATED EMBODIMENTS

It has been found that uniform, representative samples of a flowing stream of molten material can be obtained by passing a cooled, sample-collecting arm transversely through the stream. As the arm passes through the stream, molten material adheres and solidifies progressively. A sample representative of all parts of the stream is obtained. Upon emergence of the arm from the stream, the sampled material, although solidified, is still very hot. As the solidified sample cools, it contracts, cracks, breaks apart, and falls away from the arm. A sample recovery bin located under the emergent arm is a preferred way to collect the broken pieces of the sample as they fall away from the arm.

The invention is specifically illustrated in two of its presently preferred forms as adapted to particular circumstances in the sampling of slag in the copper industry. Slag from various types of furnaces in which the metallurgical materials are processed is often discharged into a launder for flow to a location of disposal or use. As such location is usually below the floor supporting the furnace, it is convenient to let the molten slag flow from the receiving launder through a hole in the floor, into a second launder or directly into a receiving vessel for transport or processing. The discharge end of the receiving launder becomes a convenient point at which to take samples of the flowing slag.

Figure 1:
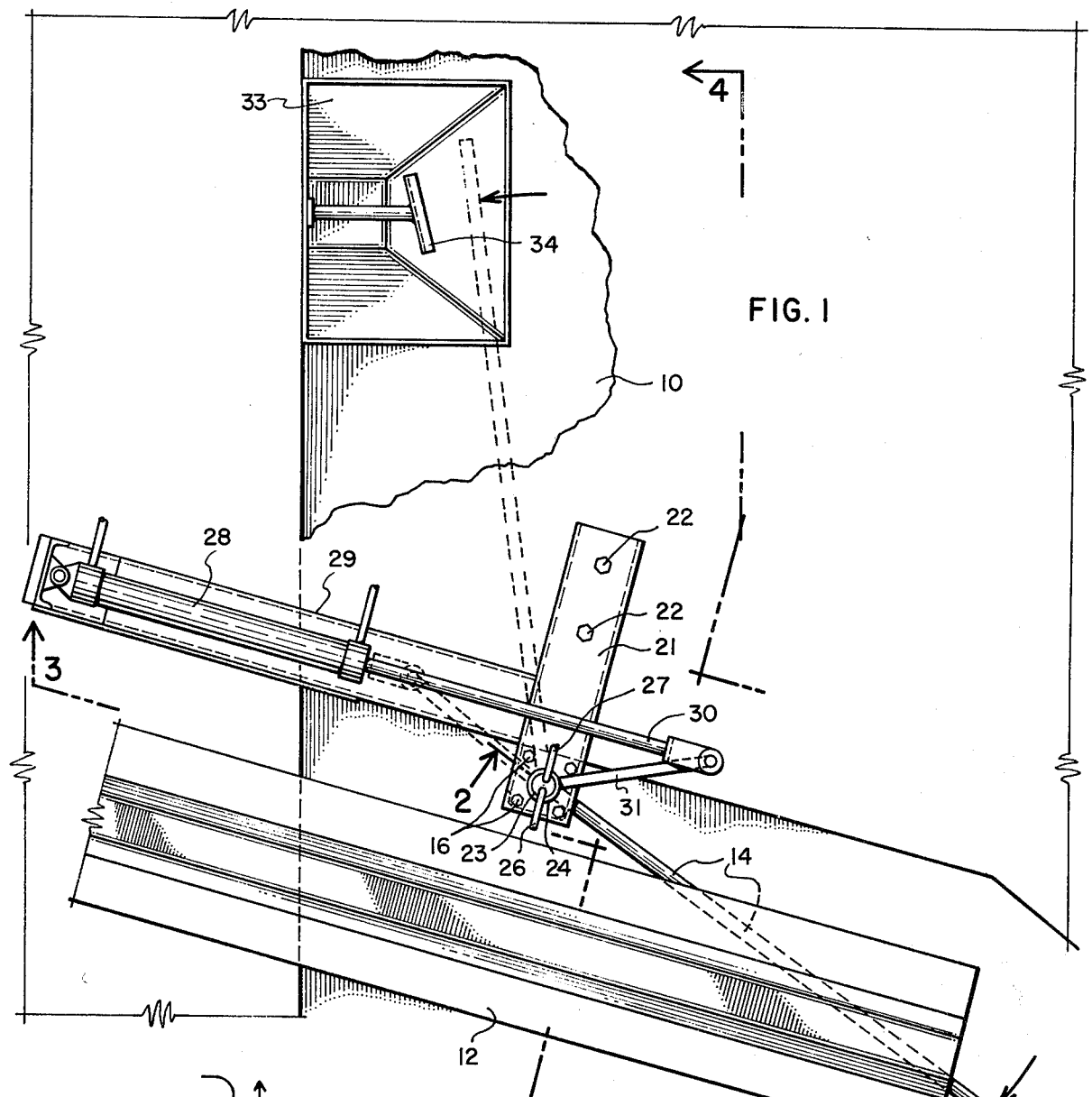
FIG. 1 is a top plan view of the apparatus as installed for periodically taking samples of molten slag or the like discharging from a launder.
Figure 2:
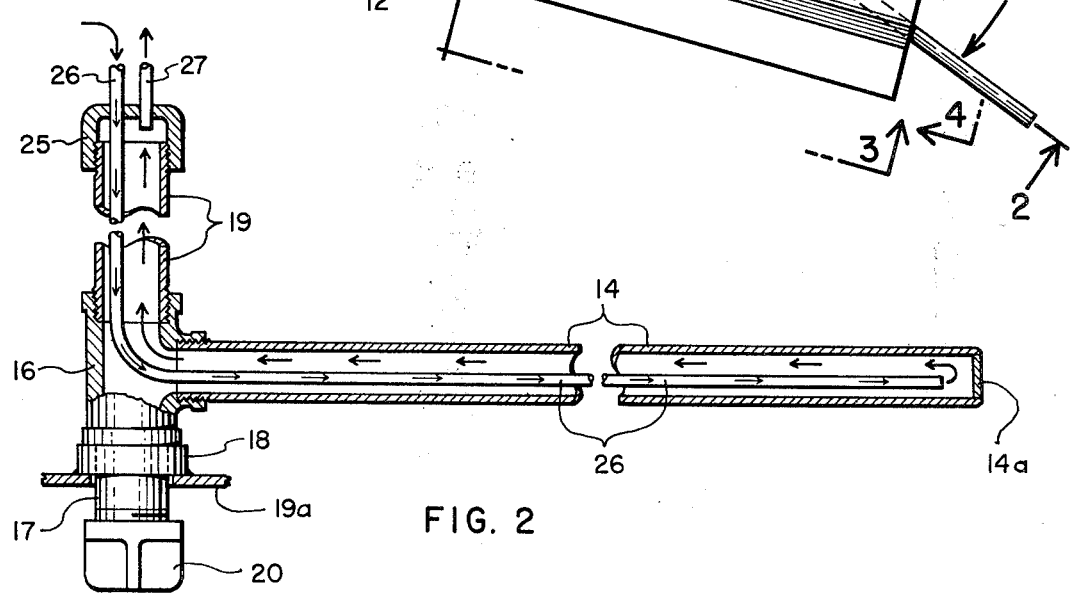
FIG. 2, a fragmentary, vertical, axial section through the sampling arm and its pivot mounting as taken on the line 2—2 of FIG. 1.
Figure 3:
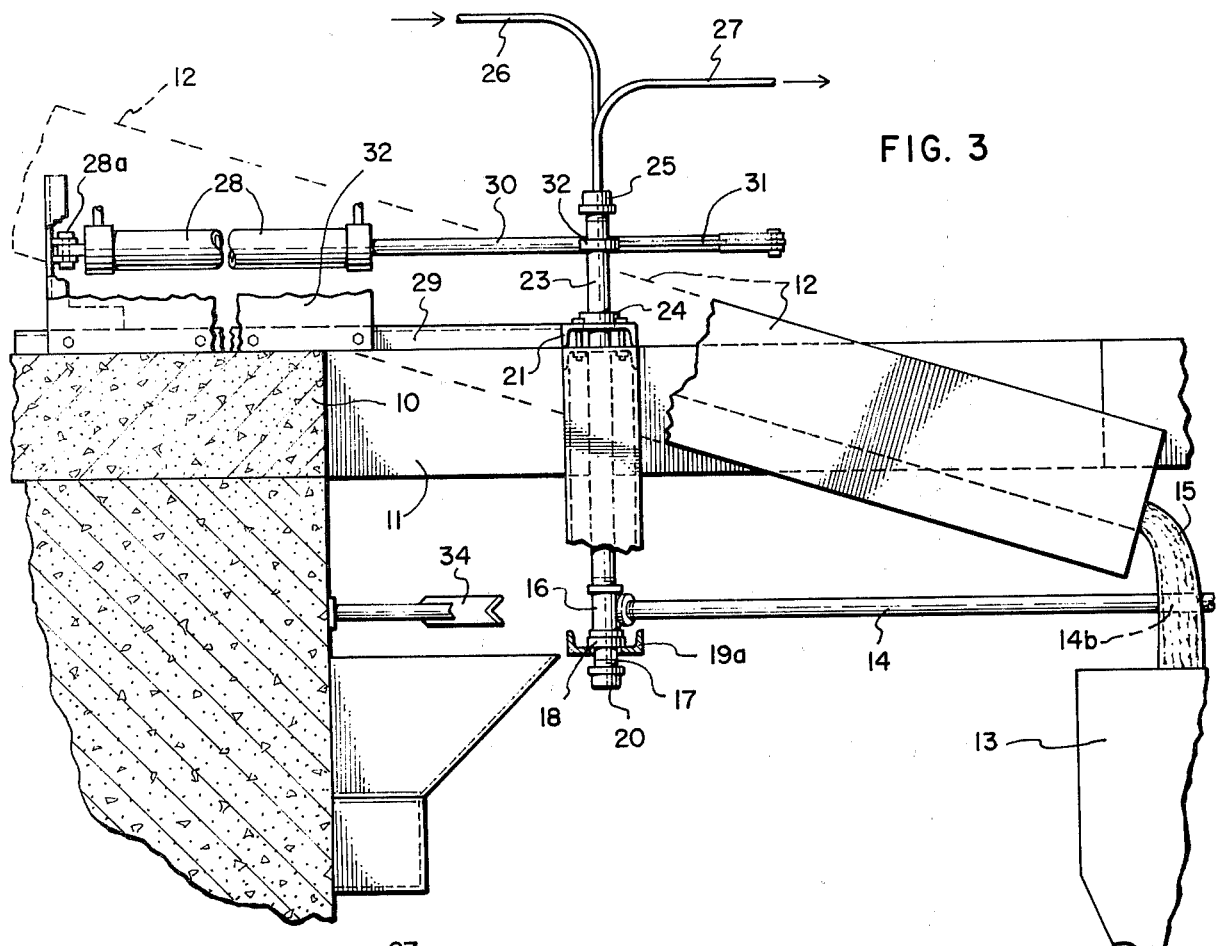
FIG. 3, a side elevation partly in vertical section taken on the line 3—3 of FIG. 1, portions being broken away for convenience of illustration.

FIGS. 1 through 4 illustrate sampling apparatus of the invention installed on a concrete floor 10 adjacent to a hole 11, FIG. 3, through which a slag-carrying launder 12 discharges into a slag-carrying railroad car 13. The sampling apparatus extends through the hole 11, its sampling arm 14 being arranged to swing horizontally through the stream 15 of molten slag discharging from launder 12.

In the form illustrated, sampling arm 14 is a length of pipe that is closed at one end by a plug 14a, FIG. 2, welded into place. The other end of the pipe is screwed into a pipe tee 16, which is part of a pivotal mounting for such sampling arm 14. The pivotal mounting includes a short length of pipe 17 screwed into and extending downwardly from pipe tee 16 through a collar 18 and the lower end 19a of a supporting frame 14 made up of structural steel channels. The lower end of pipe 17 is closed by a cap 20.

Figure 4:
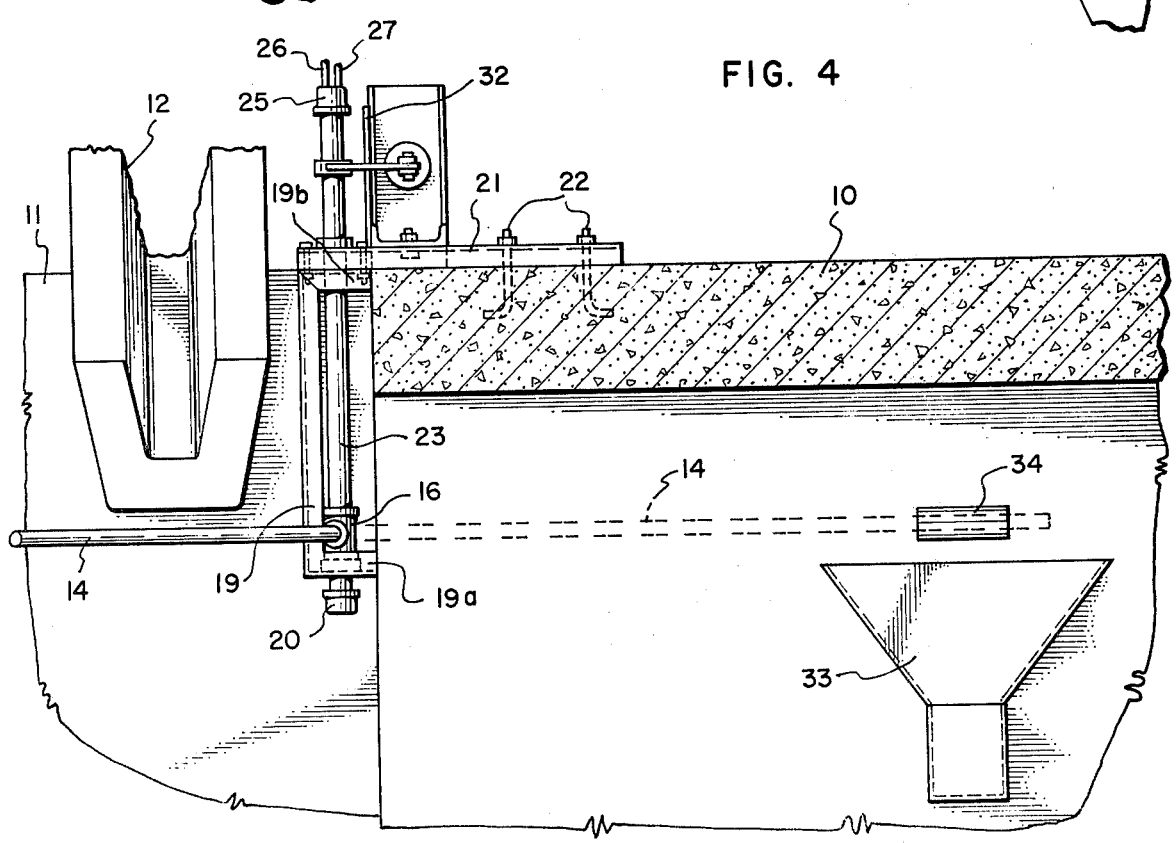
FIG. 4, a similar view in front elevation taken on the line 4—4 of FIG. 1.

The upper end 19b of frame 19 is fastened, as by bolting, see FIG. 4, to an end of a structural steel channel 21 which overhangs hole 11, the channel proper lying on and being secured to floor 10 by bolts 22 that are embedded in and protrude upwardly from the concrete of such floor.

The pivotal mounting for sampling arm 14 also includes a pipe 23 screwed into and extending upwardly from pipe tee 16 through the upper end 19b of frame 19, the overhanging end of channel 21, and a bearing collar 24 carried by such channel.

The upper end of pipe 23 is closed by a cap 25, through which in the form illustrated extend flexible tubes 26 and 27 for circulating cold water through the interior of the pipe.

Sampling arm 14 is swung back and forth on its pivotal mounting as an axis by power means, comprising in this instance a pneumatically or hydraulically activated power cylinder and piston assembly 28, FIGS. 1 and 3, pivotally mounted at 28a on structural steel channel 29 that intersects and is welded to channel 21. Reciprocating piston rod 30 has its free end pivotally secured to the free end of a lever arm 31, whose other end is rigidly secured by a collar 32 to pipe 23.

A shield 32 is preferably attached to channel 29 so as to extend upwardly between power assembly 28 and slag launder 12. This protects the power assembly from heat, possible splashes of slag, and other adverse effects of its location adjacent to the slag launder.

Power assembly 28 and lever arm 31 are arranged so that, at full extension of the piston rod 30, the effective portion 14b of sample arm 14 will have passed completely through stream 15 of molten slag discharging from launder 12, and, at full retraction, such effective portion will have returned through stream 15 and will be positioned over a sample-recovery bin 33. An abutment stop 34 is preferably provided just beyond the point of full retraction to limit any tendency for the sample arm to bow backwardly due to momentum.

In operation, cold water enters sampling arm 14 through tube 26, which terminates near the capped free end 14a thereof. On the return flow, water fills the sampling arm and its pivotal mounting and exits at cap 25 by way of tube 27. In cutting through the stream 15 of molten slag on both the forward swing and the return swing, the effective portion 14b picks up molten slag, which rapidly solidifies as a coating constituting a representative sample. The sample normally builds up on the top and sides of the sampling arm, with very little if any of the material extending across the bottom of the arm.

After sampling arm 14 comes to rest with its effective portion 14b over sample hopper 33 and the solidified slag sample continues to cool, such solidified sample will contract, crack, and break apart, the pieces falling into hopper 33.

The embodiment of FIGS. 5 through 8 is installed in a somewhat different type of slag flow system. Slag flows down a launder 38 through a hole 39 in floor 40 and discharges into a second launder 41. The transfer from the first launder to the second takes place essentially between the top and bottom of the floor, with very little space between the launders. This makes it advisable to provide apparatus having a sampling arm that swings downwardly and upwardly rather than horizontally, i.e. that pivots on a horizontal rather than a vertical axis.

The sampling arm 42, corresponds essentially to the arm 14 and has a pivotal mounting that is essentially similar except disposed on a horizontal axis. Thus, the pipe 43, FIG. 8, that is screwed into and extends from one end of pipe tee 44, is journaled in bearings 45 and 46 carried by the uprights 47a and 47b of a structural steel channel U-frame 47. Such frame 47 rests on floor 40 and is secured, as by welding, to an elongate structural steel channel 48, FIGS. 5 and 6, that is secured to floor 40 by embedded bolts 49. A short pipe 50 and cap 51 close the other end of pipe tee 44, and accommodate flexible tubes 52 and 53, which circulate coolant through the hollow interior of sampling arm 42.

A power cylinder and piston assembly 54 serves to rotate the pivoted mounting back and forth through lever arm 55 affixed to pipe 43, the cylinder of such assembly being pivotally secured to a frame member 56 upstanding from securement as by welding, to the otherwise free end of channel 48.

Figure 5:
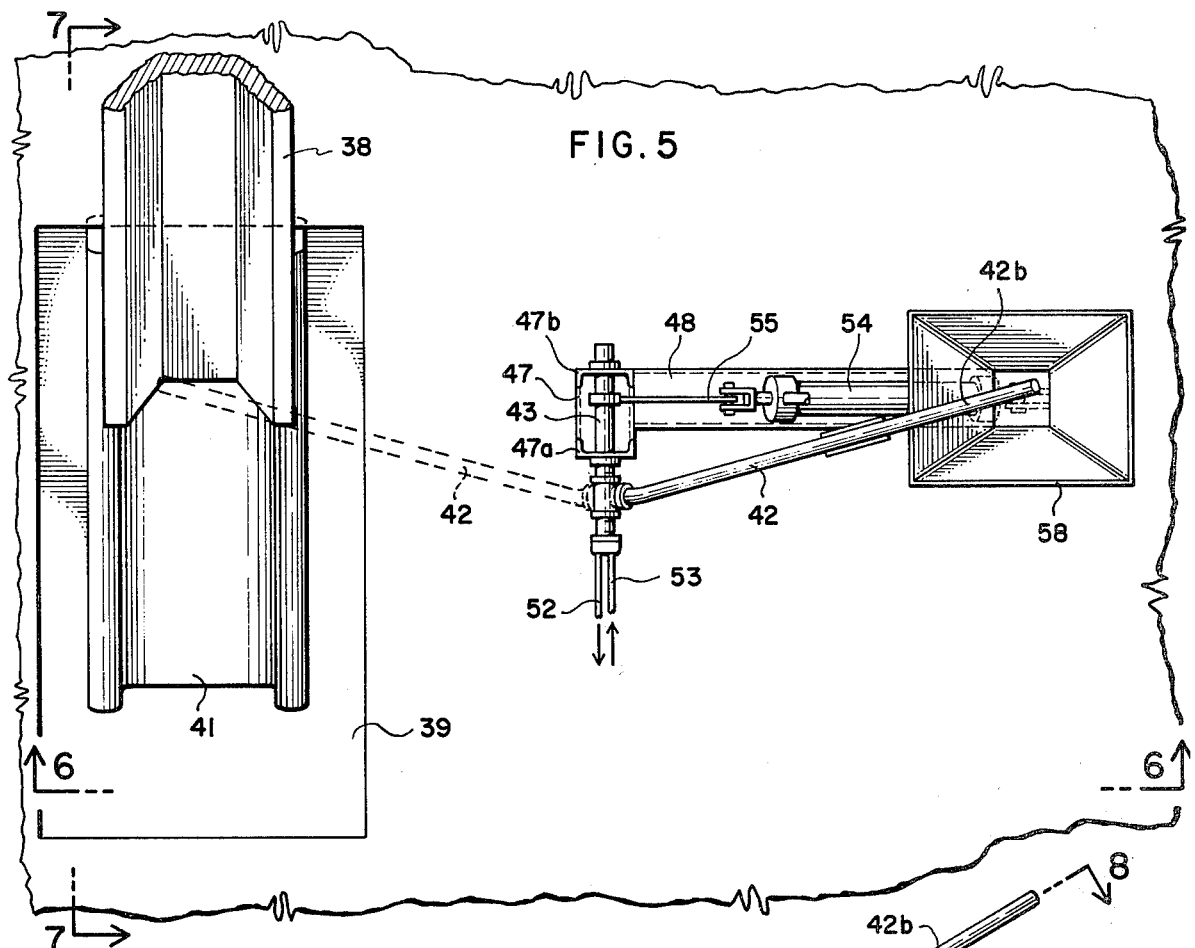
FIG. 5, a view corresponding to that of FIG. 1, but showing a somewhat different embodiment of the invention.
Figure 6:
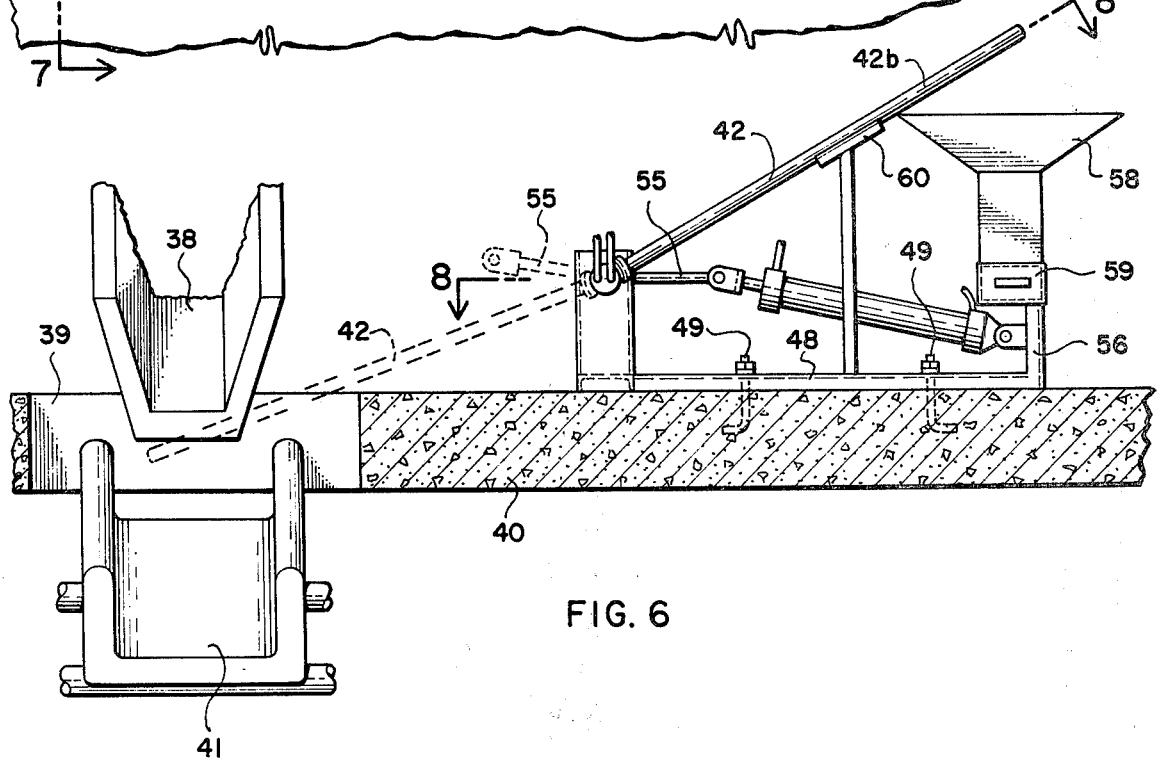
FIG. 6, a view corresponding to that of FIG. 4 but taken on the line 6—6 of FIG. 5.
Figure 7:
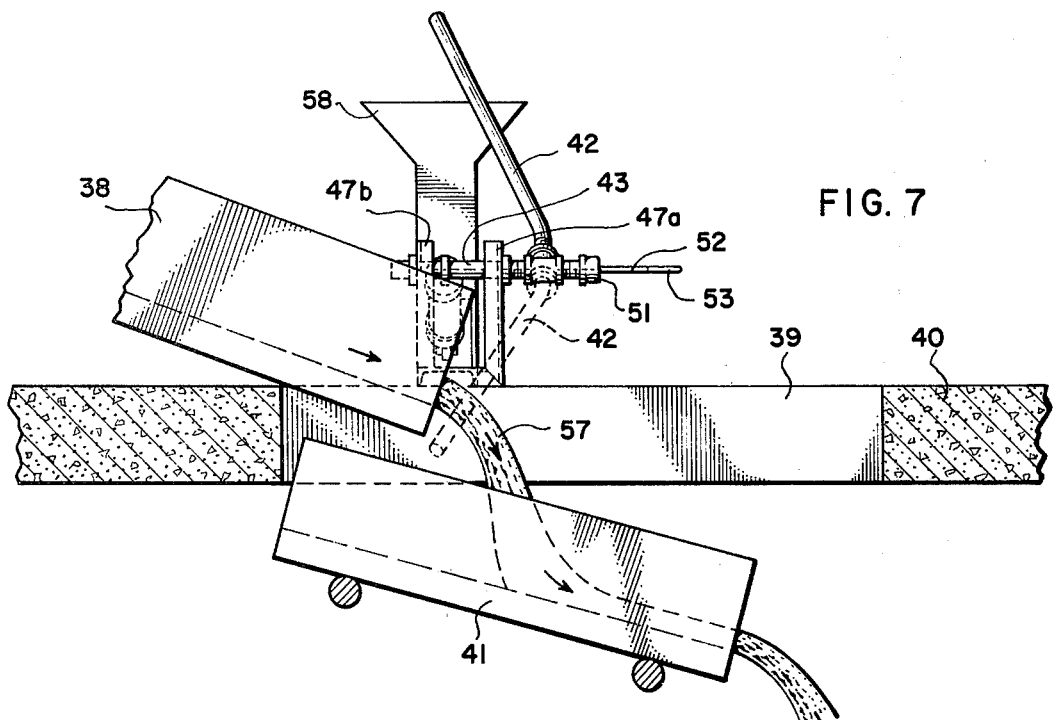
FIG. 7, a view corresponding to that of FIG. 3 but taken on the line 7—7 of FIG. 5.

As so arranged, sampling arm 42 swings downwardly and upwardly through the stream 57, FIG. 7, of molten slag discharging from launder 38 into launder 41, coming to rest with its effective portion 42b over sample recovery bin 58, see FIGS. 5 and 6, as carried by frame member 56. In this instance, a drawer 59 at the bottom of bin 58 collects the samples and provides easy access thereto.

A sample arm stop 60 prevents the arm from hitting the bin when in rest position.

Figure 8:
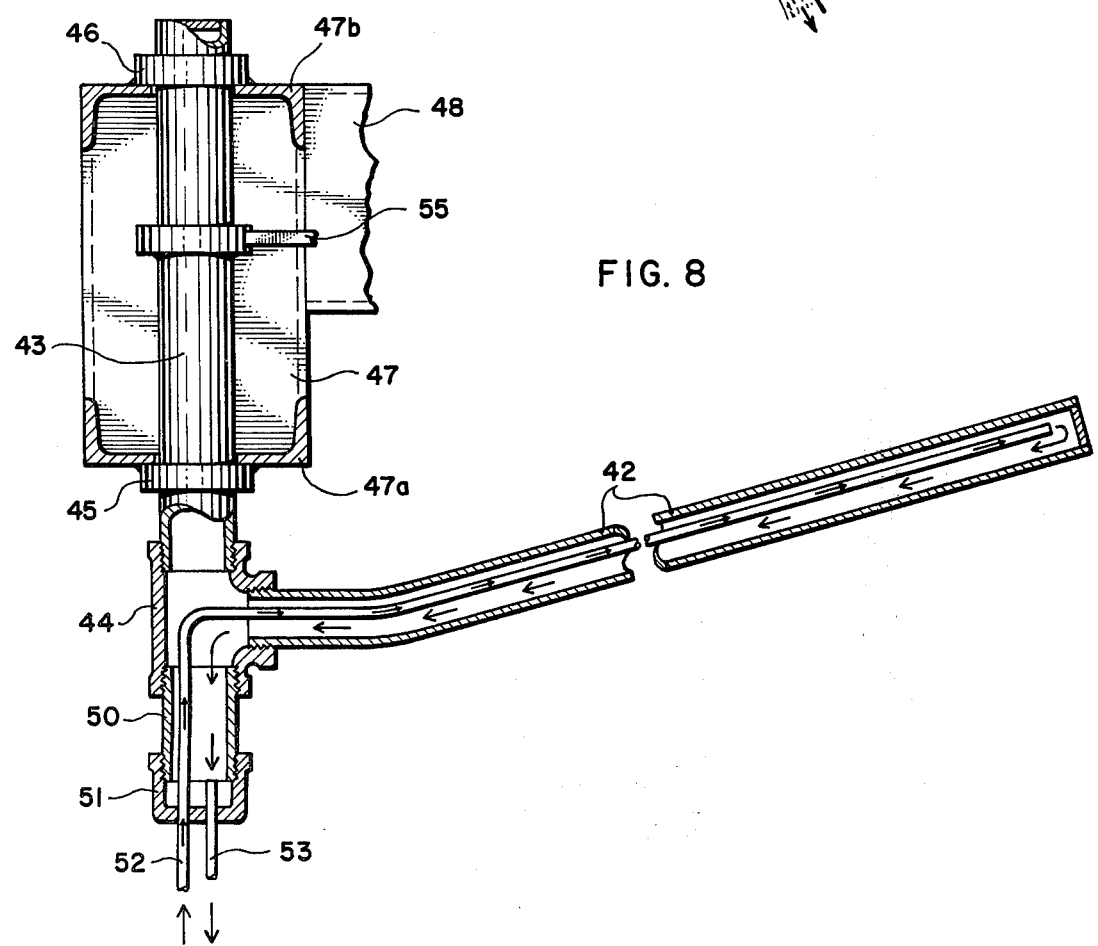
FIG. 8, a view corresponding to that of FIG. 2 but in horizontal section taken on the line 8—8 of FIG. 6.

Sampling arm 42 has a slight bend intermediate its length, as indicated in FIG. 8, so that the effective end portion thereof does not extend perpendicularly to the axis of rotation, along pipe 43. This bend is necessary so that the sampling arm can follow the inclined end face of launder 38, which is normally at right angles to its length. This enables representative samples to be taken by cutting through the stream substantially at right angles thereto, as is desirable.

The apparatus of the invention has been successfully operated under conditions of slag temperature within a range of from about 2,200° to 2,400° F. and coolant water temperature within ranges of from about 40° to 100° F., operating speed of sampling strokes being such that the stream of molten slag is completely cut through in slightly less than a second. The sampling period is not critical. Several seconds of cutting time have been used successfully.

Cooling of the arm is important for two reasons. Without the cooling, the sample arm is very rapidly heated to deformation and even melting temperature. This can occur in less than a second. With cooling, the arm can remain in the material stream for many seconds without adverse effect. Periods of 15 to 20 seconds have been tried successfully. However, unduly long sampling periods are not desirable, because the most uniform samples have been obtained in sample periods of less than 1 second. Cooling of the sample from the arm outwardly promotes both uniformity of sampling and effective freeing of the sample from the sampling arm.

In the sampling of molten materials, it is usually desirable to take samples at various time intervals during material flow. Thus, a sample is taken at the beginning of material flow and at specified time intervals, usually every few minutes, during the continuance of flow. The sampling operation may be manually initiated and reinitiated at desired intervals, but, preferably, an automatic system is provided to sense the start of material flow, initiate sampling, and repeat the sampling periodically.

For the purpose of initiating sampling it has been found desirable to employ a sensing element responsive to light given off by the molten material. Such a sensing element is so located as to sense the presence of molten material in the launder, thereby initiating the sampling operation. Subsequent cycles are controlled by a timer during continuance of flow of the molten material, power being shut off by the sensing element when molten material is no longer flowing.

Whereas this invention is here illustrated and described with respect to preferred embodiments thereof, it would be understood that various changes may be made without departing from the inventive concepts as claimed.

I claim:
1. A method of sampling a stream of molten material, comprising the steps of passing a sampling arm through the stream; passing a coolant through the arm so as to continually cool the arm as it passes through the stream, whereby such arm will pick up a coating of molten material and solidify it as a sample; holding the sample arm over a sample collecting area for a time sufficient for the sample to cool, contract, break apart and fall away from the arm; and recovering the sample by collecting pieces of the solidified coating as it contracts, breaks apart, and falls away from the arm.

2. A method in accordance with claim 1, wherein the sampling arm is moved at timed intervals during material flow.

3. a method according to claim 2, wherein movement of the sampling arm is initiated upon flow of the molten material.

4. Apparatus for sampling a stream of molten material, comprising a sampling arm; means for passing the arm through a stream of molten material; means for passing a coolant through the arm so as to continually cool the arm as it passes through the stream, whereby such arm will pick up molten material and solidify it as a sample; and means for holding the sample arm over a sample collection area for a time sufficient for the sample to cool, contract, break apart and fall away from the arm into the collection area.

5. Apparatus in accordance with claim 4, wherein the recovery means is a bin arranged to receive the adherant material as it falls from the sample arm.

6. Apparatus in accordance with claim 4, wherein the sampling arm is pivotally mounted, and the means for moving the cooled arm is a power cylinder and piston assembly and linkage adapted to swing the arm back and forth.

7. Apparatus in accordance with claim 6, wherein the sampling arm is arranged to be swung from a position over the receiving means, through the stream of molten material, and back through the stream of molten material to its starting point over the recovery means.

* * * * *